United States Patent

Yoon

(10) Patent No.: US 9,470,168 B2
(45) Date of Patent: Oct. 18, 2016

(54) APPARATUS AND METHOD FOR DIAGNOSING DETERIORATION OF OXYGEN SENSOR OF VEHICLE

(71) Applicant: Hyundai Motor Company, Seoul (KR)

(72) Inventor: Sang Il Yoon, Whasung-Si (KR)

(73) Assignee: Hyundai Motor Company, Seoul (KR)

( * ) Notice: Subject to any disclaimer, the term of this patent is extended or adjusted under 35 U.S.C. 154(b) by 287 days.

(21) Appl. No.: 14/327,345

(22) Filed: Jul. 9, 2014

(65) Prior Publication Data

US 2015/0184609 A1 Jul. 2, 2015

(30) Foreign Application Priority Data

Dec. 26, 2013 (KR) .................. 10-2013-0163787

(51) Int. Cl.
| | |
|---|---|
| *F02D 41/14* | (2006.01) |
| *F02D 41/22* | (2006.01) |
| *G01N 33/00* | (2006.01) |
| *F02D 41/00* | (2006.01) |
| *F02D 41/18* | (2006.01) |

(52) U.S. Cl.
CPC ......... *F02D 41/222* (2013.01); *F02D 41/0072* (2013.01); *F02D 41/1495* (2013.01); *G01N 33/007* (2013.01); *F02D 41/1454* (2013.01); *F02D 41/18* (2013.01); *Y02T 10/47* (2013.01)

(58) Field of Classification Search
CPC ............ F02D 41/0072; F02D 41/222; F02D 41/1495; F02D 2041/0075; G01N 33/007; Y02T 10/47; F01N 2560/025; G01M 15/104; G01M 15/05
USPC .......................................... 701/108, 109, 114
See application file for complete search history.

(56) References Cited

U.S. PATENT DOCUMENTS

| | | | | |
|---|---|---|---|---|
| 4,402,217 A | * | 9/1983 | Higashiyama ........ | G01M 15/05 73/114.61 |
| 7,861,515 B2 | * | 1/2011 | Brahma .............. | F02D 41/1495 60/277 |
| 8,240,188 B2 | * | 8/2012 | Umehara ............. | F01N 3/0222 73/23.2 |
| 2009/0013665 A1 | * | 1/2009 | Brahma ................ | F02D 41/221 60/276 |
| 2011/0011153 A1 | * | 1/2011 | Umehara ............. | F01N 3/0222 73/23.31 |
| 2011/0011378 A1 | * | 1/2011 | Nakamura ............ | F02M 26/49 123/568.16 |
| 2011/0054763 A1 | * | 3/2011 | Oehlerking ......... | F02D 41/0007 701/108 |
| 2012/0265396 A1 | * | 10/2012 | Makki ................. | F02D 41/1495 701/30.8 |
| 2013/0073179 A1 | * | 3/2013 | Song ................... | F02D 41/0072 701/102 |
| 2014/0130785 A1 | * | 5/2014 | Levijoki ............. | F02D 41/1441 123/703 |

FOREIGN PATENT DOCUMENTS

| | | | | |
|---|---|---|---|---|
| JP | 2503742 B2 | | 4/1996 | |
| JP | WO 2009118605 A1 | * | 10/2009 | ......... F02D 41/1495 |
| KR | 1019980038809 A | | 8/1998 | |
| KR | 10-0612967 B1 | | 8/2006 | |

* cited by examiner

*Primary Examiner* — Peter Macchiarolo
*Assistant Examiner* — Nathaniel Kolb
(74) *Attorney, Agent, or Firm* — Morgan, Lewis & Bockius LLP

(57) ABSTRACT

A method of diagnosing deterioration of an oxygen sensor of a vehicle may include detecting a first exhaust gas recirculation (EGR) amount by a mass air flow (MAF) sensor, detecting a second EGR amount by the oxygen sensor, comparing a first difference between the first EGR amount and the second EGR amount with a first predetermined value in a first predetermined operating region, and determining that the oxygen sensor may be in danger of the deterioration when the first difference between the first EGR amount and the second EGR amount may be greater than or equal to the first predetermined value in the first predetermined operating region.

19 Claims, 3 Drawing Sheets

APPARATUS AND METHOD FOR DIAGNOSING DETERIORATION OF OXYGEN SENSOR OF VEHICLE

CROSS-REFERENCE TO RELATED APPLICATION

The present application claims priority to Korean Patent Application No. 10-2013-0163787 filed Dec. 26, 2013, the entire contents of which is incorporated herein for all purposes by this reference.

BACKGROUND OF THE INVENTION

1. Field of the Invention

The present invention relates to an apparatus and a method for diagnosing deterioration of an oxygen sensor of a vehicle. More particularly, the present invention relates to an apparatus and a method that diagnoses deterioration of the oxygen sensor when a difference between an exhaust gas recirculation (EGR) amount detected by a mass air flow (MAF) sensor and an exhaust gas recirculation (EGR) amount detected by an oxygen sensor occurs.

2. Description of Related Art

Generally an oxygen sensor is mounted on a vehicle for adjusting an air-fuel ratio by determining a mixing ratio between air and a fuel in a combustion chamber of an engine.

The oxygen sensor performs air-fuel ratio control by detecting an oxygen content amount among exhaust gas and determining a fuel mixing ratio. Thus, fuel consumption is improved and exhaust gas is reduced.

Meanwhile, a mass air flow (MAF) sensor which detects an intake air amount drawn into the engine is mounted on the vehicle to operate the engine appropriately.

Generally, an exhaust gas recirculation (EGR) system is provided to a vehicle for reducing noxious exhaust gases of the vehicle. The amount of nitrogen oxide in the exhaust gas is increased in an oxygen rich air mixture, and the air mixture is combusted well. Therefore the exhaust gas, as a consequence of a part of the exhaust gas being recirculated to the air mixture in order to reduce the oxygen ratio in the air mixture, hinders combustion.

The MAF sensor and the oxygen sensor that are mounted on the vehicle as stated above control an exhaust gas recirculation (EGR) amount. That is, a controller controls the EGR amount by measuring the intake air by the MAF sensor before activating the oxygen sensor, and on the contrary, the controller controls the EGR amount by detecting the oxygen content of the exhaust gas by the oxygen sensor after activating the oxygen sensor.

If the oxygen sensor does not detect the oxygen amount among exhaust gas on account of deterioration or malfunction, the controller can't control a fuel amount supplied to the engine cylinder. Thus, the exhaust gas may include harmful components.

The information disclosed in this Background section is only for enhancement of understanding of understanding of the general background of the invention and should not be taken an acknowledgement or any form of suggestion that this information forms the prior art already known to a person skilled in the art.

BRIEF SUMMARY

Various aspects of the present invention are directed to providing an apparatus and method of diagnosing deterioration of an oxygen sensor of a vehicle having advantages of diagnosing deterioration of the oxygen sensor when a difference between an exhaust gas recirculation (EGR) amount detected by a mass air flow (MAF) sensor and an exhaust gas recirculation (EGR) amount detected by an oxygen sensor occurs in a predetermined operating region.

In an aspect of the present invention, a method of diagnosing deterioration of an oxygen sensor of a vehicle, may include detecting a first exhaust gas recirculation (EGR) amount by a mass air flow (MAF) sensor, detecting a second EGR amount by the oxygen sensor, comparing a first difference between the first EGR amount and the second EGR amount with a first predetermined value in a first predetermined operating region, and determining that the oxygen sensor is in danger of the deterioration when the first difference between the first EGR amount and the second EGR amount is greater than or equal to the first predetermined value in the first predetermined operating region.

When the oxygen sensor is determined to be in the danger of the deterioration, the method may further include comparing a second difference between the first EGR amount and the second EGR amount with a second predetermined value in a second predetermined operating region, and diagnosing deterioration of the oxygen sensor when the second difference between the first EGR amount and the second EGR amount is greater than or equal to the second predetermined value in the second predetermined operating region.

The first predetermined operating region is a region where the oxygen sensor begins to be activated.

The first predetermined operating region is determined depending on an engine speed and a fuel amount.

The second predetermined operating region is a region where the oxygen sensor is completely activated.

The second predetermined operating region is a region determined after the oxygen sensor is activated, wherein the second predetermined operating region is determined depending on an engine speed and a fuel amount.

When the deterioration of the oxygen sensor is diagnosed, the method may further include outputting a signal for limiting engine power.

When the deterioration of the oxygen sensor is diagnosed, the method may further include sending a warning to a display unit.

In another aspect of the present invention, a method of diagnosing deterioration of an oxygen sensor of a vehicle, may include detecting a first exhaust gas recirculation (EGR) amount by a mass air flow (MAF) sensor, detecting a second exhaust gas recirculation (EGR) amount by the oxygen sensor in two or more predetermined regions, and determining whether there is the deterioration of the oxygen sensor by comparing the first EGR amount with the second EGR amount in each of the two or more predetermined regions.

When a difference between the first EGR amount and the second EGR amount is greater than or equal to each of two or more predetermined values in each of the two or more predetermined regions, the method may include diagnosing the deterioration of the oxygen sensor.

The two or more predetermined regions are determined according to an engine speed and a fuel amount.

When the deterioration of the oxygen sensor is diagnosed, the method may further include outputting a signal for limiting engine power.

When the deterioration of the oxygen sensor is diagnosed, the method may further include sending a warning to a displayer.

In further another aspect of the present invention, an apparatus for diagnosing deterioration of an oxygen sensor of a vehicle, may include a mass air flow (MAF) sensor detecting an intake air amount drawn into an engine, the oxygen sensor detecting an oxygen amount in an exhaust gas, and a controller determining whether there is the deterioration of the oxygen sensor by comparing a first exhaust gas recirculation (EGR) amount detected by the MAF sensor with a second exhaust gas recirculation (EGR) amount detected by the oxygen sensor at a predetermined region.

The apparatus may further include a displayer sending a warning to a driver when the deterioration of the oxygen sensor is diagnosed.

The predetermined region may include two or more predetermined regions, wherein the controller compares the first EGR amount detected by the MAF sensor with the second EGR amount detected by the oxygen sensor in the two or more predetermined regions.

The controller diagnoses the deterioration of the oxygen sensor when a difference between the first EGR amount and the second EGR amount is greater than or equal to each of two or more predetermined values in the two or more predetermined regions.

The two or more predetermined regions are determined according to an engine speed and a fuel amount.

According to exemplary embodiments of the present invention as described above, deterioration of the oxygen sensor is diagnosed more precisely so that reliability of controlling an EGR amount can be improved.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
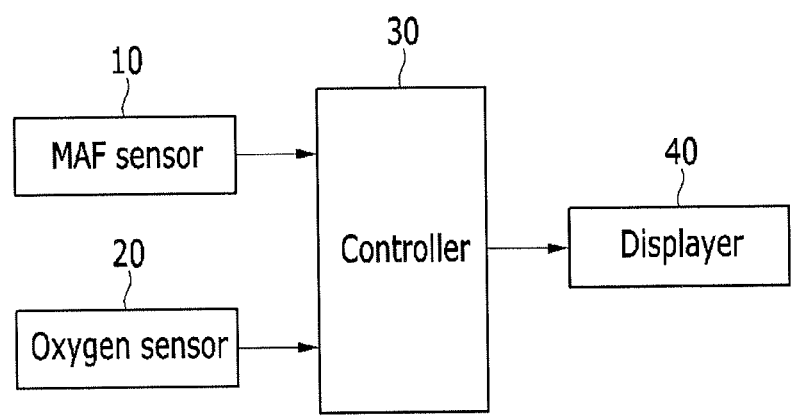
FIG. 1 is a block diagram of an apparatus of diagnosing deterioration of an oxygen sensor of a vehicle according to an exemplary embodiment of the present invention.

Reference numerals set forth in the Drawings include reference to the following elements as further discussed below:

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, an exemplary embodiment of the present invention will be described with reference to the accompanying drawings so that those skilled in the Field of the Invention to which the present invention pertains may carry out the exemplary embodiment.

FIG. 1 is a block diagram of an apparatus for diagnosing deterioration of an oxygen sensor of a vehicle according to an exemplary embodiment of the present invention.

As shown in FIG. 1, an apparatus for diagnosing deterioration of an oxygen sensor may include a mass air flow (MAF) sensor 10, an oxygen sensor 20, a controller 30, and a display unit 40.

The MAF sensor 10 detects an intake air amount drawn into the engine cylinder. The MAF sensor 10 may include a heating element using a sensing resistor or heating resistor to detect an amount of air flow depending on a temperature of the heating element. The MAF sensor 10 outputs the intake air amount detected according to the amount of air flow to controller 30.

The MAF sensor 10 additionally detects an exhaust gas recirculation (EGR) amount from the intake air amount drawn into the engine.

The oxygen sensor 20 detects an oxygen amount in an exhaust gas generated after combustion, and outputs a signal to the controller 30. The oxygen sensor 20 may determine an EGR amount from the oxygen amount.

The controller 30 receives the first EGR amount detected by the MAF sensor 10 and the second EGR amount detected by the oxygen sensor 20, and determines deterioration of the oxygen sensor 20 by comparing the first EGR amount with the second EGR amount at a predetermined region.

The controller 30 compares the first EGR amount detected by the MAF sensor 10 with the second EGR amount detected by the oxygen sensor 20, and diagnoses deterioration of the oxygen sensor 20 when a difference between the first EGR amount and the second EGR amount is greater than or equal to each of predetermined values in two or more predetermined regions.

In an aspect of the present invention, the controller 30 may be implemented as at least one processor that is operated by a predetermined program, and the predetermined program may be programmed in order to perform each step of a method of diagnosing deterioration of an oxygen sensor of the vehicle.

The display unit 40 may send a warning to a driver when receiving a signal from the controller 30 when the deterioration of the oxygen sensor 20 is diagnosed. The display unit 40 may be mounted on a cluster in front of a driver or may be included in another display device.

Figure 2:
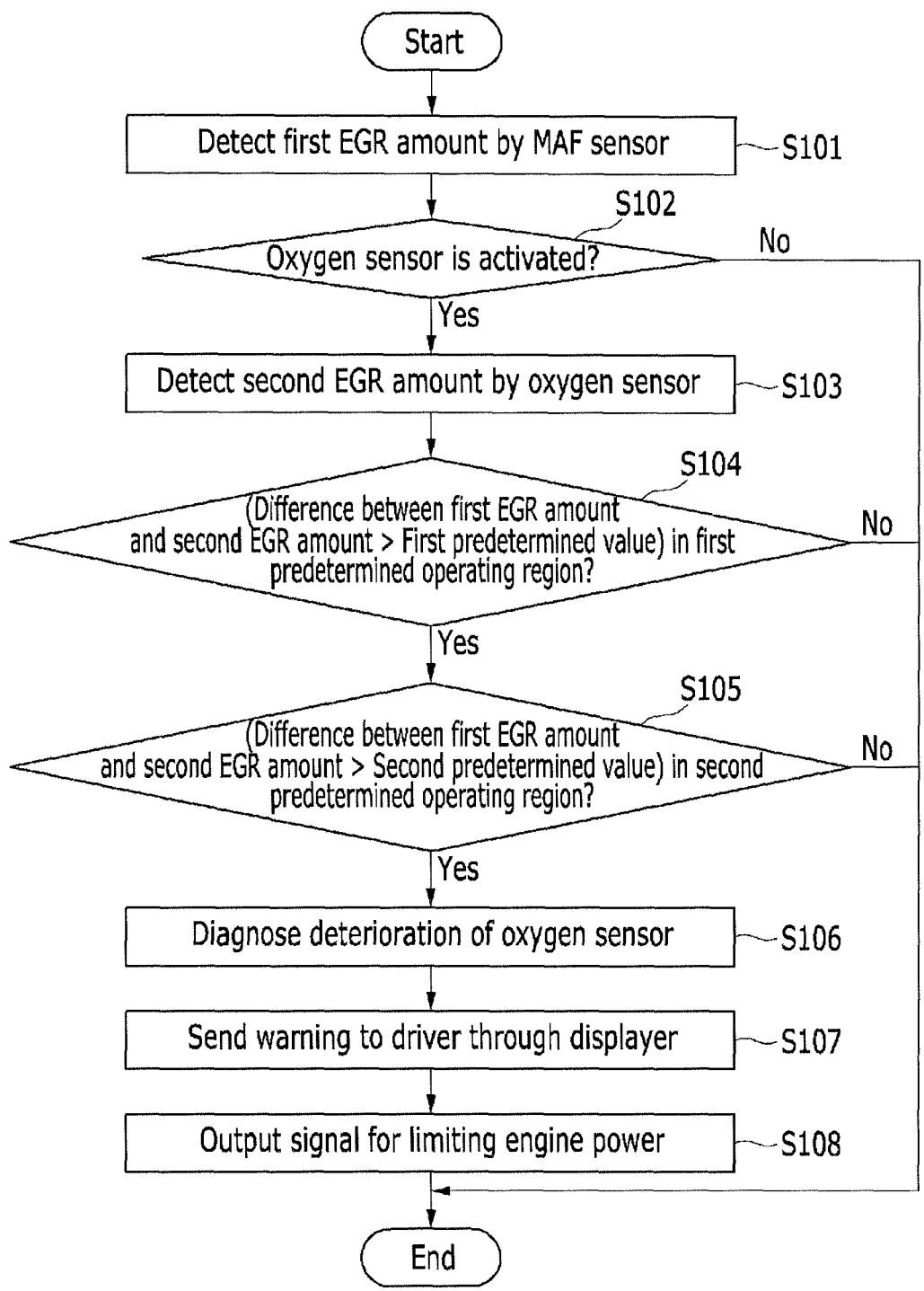
FIG. 2 is a flowchart of a method of diagnosing deterioration of an oxygen sensor of a vehicle according to an exemplary embodiment of the present invention.

FIG. 2 is a flowchart of a method of diagnosing deterioration of an oxygen sensor of a vehicle according to an exemplary embodiment of the present invention.

As shown in FIG. 2, the method of diagnosing deterioration of the oxygen sensor of the vehicle starts with detecting a first exhaust gas recirculation (EGR) amount by the MAF sensor 10 at step S101.

The MAF sensor 10 detects the EGR amount when the oxygen sensor 20 is not activated yet when the engine is operated at a low load. Therefore, the MAF sensor 10 may be operated prior to the oxygen sensor 20 when an ignition of the vehicle is turned on.

The MAF sensor 10 may output the detected EGR amount to the controller 30.

After that, the controller 30 determines whether the oxygen sensor 20 is activated at step S102.

If the oxygen sensor 20 is not activated at step S102, the method of diagnosing the oxygen sensor of the vehicle ends because the oxygen sensor 20 does not determine the EGR amount.

If the oxygen sensor 20 is activated at step S102, the controller 30 detects a second EGR amount by the oxygen sensor 20 at step S103.

If the first EGR amount is detected by the MAF sensor 10 at step S101 and the second EGR amount is detected by the oxygen sensor 20 at step S103, the controller 30 compares a difference between the first EGR amount and the second EGR amount with a first predetermined value in a first predetermined operating region at step S104.

If the difference between the first EGR amount and the second EGR amount is greater than or equal to the first predetermined value in the first predetermined operating region, the controller 30 determines that the oxygen sensor 20 is in danger of deterioration and the control process proceeds to step S105.

If the difference between the first EGR amount and the second EGR amount is less than the first predetermined value in the first predetermined operating region, the controller 30 diagnoses that the oxygen sensor 20 is not deteriorating, and the method of diagnosing the oxygen sensor of the vehicle ends.

If the oxygen sensor 20 is in danger of deterioration at step S104, the controller 30 compares the difference between the first EGR amount and the second EGR amount with a second predetermined value in a second predetermined operating region at step S105.

The controller 30 may perform step S104 in the first predetermined operating region and perform step S105 in the second predetermined operating region to diagnose deterioration of the oxygen sensor 20 more precisely.

If the difference between the first EGR amount and the second EGR amount is greater than or equal to the second predetermined value in the second predetermined operating region at step S105, the controller 30 diagnoses deterioration of the oxygen sensor 20 at step S106.

Figure 3:
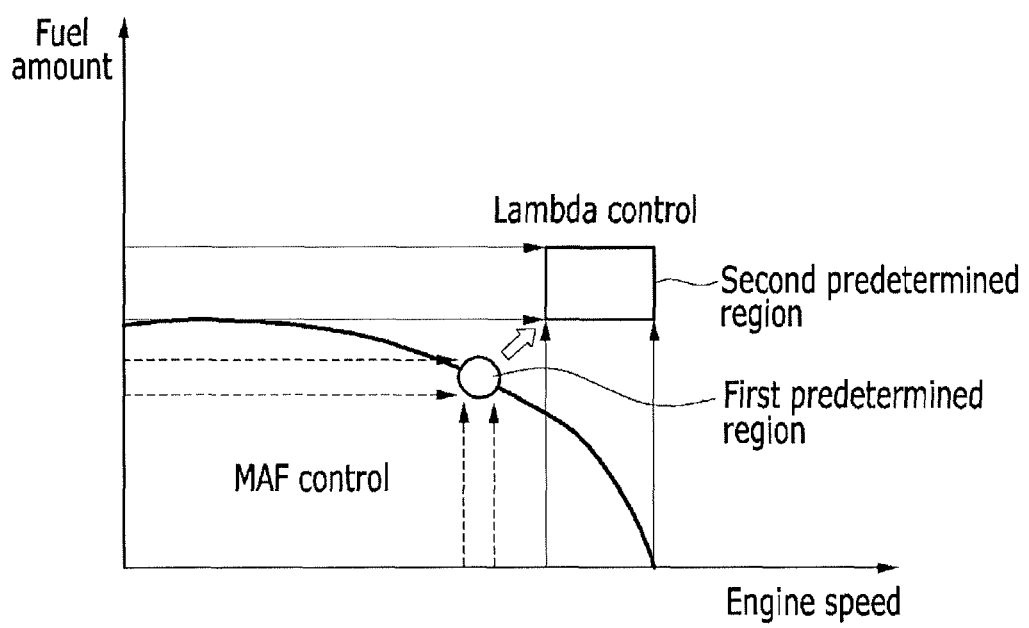
FIG. 3 is a graph showing a predetermined operating region for diagnosing deterioration of an oxygen sensor depending on an engine speed and a fuel amount supplied to an engine cylinder according to an exemplary embodiment of the present invention.

FIG. 3 is a graph showing a predetermined operating region for diagnosing deterioration of an oxygen sensor depending on an engine speed and a fuel amount.

Referring to FIG. 3, the MAF sensor 10 determines the EGR amount when the engine is operated at a low load depending on the engine speed and the fuel amount. The oxygen sensor 20 may determine the EGR amount by determining a lambda value after the oxygen sensor 20 is activated.

The first predetermined operating region may be determined depending on the engine speed and the fuel amount, and may be a region where the oxygen sensor 20 begins to be activated. In addition, the second predetermined operating region may be determined according to the engine speed and the fuel amount after the oxygen sensor 20 is activated.

In another aspect of the present invention, the second predetermined operating region may be determined according to the engine speed and the fuel amount when the oxygen sensor 20 is completely activated.

Referring back to FIG. 2, when deterioration of the oxygen sensor 20 is diagnosed at step S106, the controller 30 sends a warning to the driver through the display unit 40 at step S107. To achieve this, the controller 30 may output a warning signal to the display unit 40 and the display unit 40 may preferably send the warning to the driver by turning on a warning lamp mounted on the cluster.

In addition, the controller 30 may output a signal for limiting engine power to the Engine Control Unit (ECU) at step S108 when deterioration of the oxygen sensor 20 is diagnosed.

The controller 30 may control an air-fuel ratio and reduce the exhaust gas by limiting the engine power when deterioration of the oxygen sensor 20 is diagnosed. Therefore, deterioration of the oxygen sensor may be diagnosed more precisely so that reliability of controlling the EGR amount can be improved.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method of diagnosing deterioration of an oxygen sensor of a vehicle, comprising:
    calculating a first exhaust gas recirculation (EGR) amount using the output of a mass air flow (MAF) sensor;
    calculating a second EGR amount using the output of the oxygen sensor;
    comparing a first difference between the first EGR amount and the second EGR amount with a first predetermined value in a first predetermined operating region; and
    determining that the oxygen sensor is in danger of deterioration when the first difference between the first EGR amount and the second EGR amount is greater than or equal to the first predetermined value in the first predetermined operating region.

2. The method of claim 1, wherein, when the oxygen sensor is determined to be in the danger of deterioration, the method further comprises:

comparing a second difference between the first EGR amount and the second EGR amount with a second predetermined value in a second predetermined operating region; and diagnosing deterioration of the oxygen sensor when the second difference between the first EGR amount and the second EGR amount is greater than or equal to the second predetermined value in the second predetermined operating region.

3. The method of claim 1, wherein the first predetermined operating region is a region where the oxygen sensor begins to be activated.

4. The method of claim 3, wherein the first predetermined operating region is determined depending on an engine speed and a fuel amount.

5. The method of claim 2, wherein the second predetermined operating region is a region where the oxygen sensor is completely activated.

6. The method of claim 2, wherein the second predetermined operating region is a region determined after the oxygen sensor is activated.

7. The method of claim 6, wherein the second predetermined operating region is determined depending on an engine speed and a fuel amount.

8. The method of claim 2, wherein, when deterioration of the oxygen sensor is diagnosed, the method further comprises outputting a signal for limiting engine power.

9. The method of claim 2, wherein, when deterioration of the oxygen sensor is diagnosed, the method further comprises sending a warning to a display unit.

10. A method of diagnosing deterioration of an oxygen sensor of a vehicle, comprising:
    calculating a first exhaust gas recirculation (EGR) amount using the output of a mass air flow (MAF) sensor;
    calculating a second exhaust gas recirculation (EGR) amount using the output of the oxygen sensor in two or more predetermined operating regions; and
    determining whether there is deterioration of the oxygen sensor by comparing the first EGR amount with the second EGR amount in each of the two or more predetermined operating regions.

11. The method of claim 10, wherein, when a difference between the first EGR amount and the second EGR amount is greater than or equal to each of two or more predetermined values in each of the two or more predetermined operating regions, diagnosing that the oxygen sensor has deteriorated.

12. The method of claim 10, wherein the two or more predetermined operating regions are determined according to an engine speed and a fuel amount.

13. The method of claim 10, wherein, when it is diagnosed that the oxygen sensor has deteriorated, the method further comprises outputting a signal for limiting engine power.

14. The method of claim 10, wherein, when it is diagnosed that the oxygen sensor has deteriorated, the method further comprises sending a warning to a display unit.

15. An apparatus for diagnosing deterioration of an oxygen sensor of a vehicle, comprising:
    a mass air flow (MAF) sensor detecting an intake air amount drawn into an engine;
    the oxygen sensor detecting an oxygen amount in an exhaust gas; and
    a controller determining whether there is deterioration of the oxygen sensor by comparing a first exhaust gas recirculation (EGR) amount calculated using the output of the MAF sensor with a second exhaust gas recirculation (EGR) amount calculated using the output of the oxygen sensor in at least one predetermined operating region.

16. The apparatus of claim 15, further comprising a display unit sending a warning to a driver when it is diagnosed that the oxygen sensor has deteriorated.

17. The apparatus of claim 15,
    wherein the at least one predetermined operating region includes two or more predetermined operating regions; and
    wherein the controller compares the first EGR amount calculated using the output of the MAF sensor with the second EGR amount calculated using the output of the oxygen sensor in the two or more predetermined operating regions.

18. The apparatus of claim 17, wherein the controller diagnoses that the oxygen sensor has deteriorated when a difference between the first EGR amount and the second EGR amount is greater than or equal to each of two or more predetermined values in the two or more predetermined operating regions.

19. The apparatus of claim 15, wherein the two or more predetermined operating regions are determined according to an engine speed and a fuel amount.

* * * * *